United States Patent
Pruente et al.

(10) Patent No.: US 9,513,275 B2
(45) Date of Patent: Dec. 6, 2016

(54) SYSTEM AND PROCESS OF UTILIZING OIL QUALITY ANALYSIS AND DISSOLVED GAS ANALYSIS TO DETECT EARLY STAGE PROBLEMS IN OIL FILLED ELECTRICAL APPARATUSES

(71) Applicant: Waukesha Electric Systems, Inc., Waukesha, WI (US)

(72) Inventors: John Pruente, Keller, TX (US); Nuwan Rodrigo, Little Elm, TX (US)

(73) Assignee: Waukesha Electric Systems, Inc., Waukesha, WI (US)

(*) Notice: Subject to any disclaimer, the term of this patent is extended or adjusted under 35 U.S.C. 154(b) by 73 days.

(21) Appl. No.: 14/209,759

(22) Filed: Mar. 13, 2014

(65) Prior Publication Data
US 2014/0260529 A1  Sep. 18, 2014

Related U.S. Application Data

(60) Provisional application No. 61/781,207, filed on Mar. 14, 2013.

(51) Int. Cl.
| | |
|---|---|
| G01N 33/26 | (2006.01) |
| G01N 33/18 | (2006.01) |
| G01N 33/497 | (2006.01) |
| G01M 15/00 | (2006.01) |
| G01N 33/28 | (2006.01) |

(52) U.S. Cl.
CPC .............................. *G01N 33/2888* (2013.01)

(58) Field of Classification Search
None
See application file for complete search history.

(56) References Cited

U.S. PATENT DOCUMENTS

| 3,844,160 | A  * | 10/1974 | Yamaoka ..................... 73/19.11 |
|---|---|---|---|
| 4,890,478 | A  * | 1/1990 | Claiborne et al. ........... 73/19.11 |
| 4,944,178 | A  * | 7/1990 | Inoue et al. .................. 73/19.1 |
| 6,035,706 | A  * | 3/2000 | Campagnolo et al. ...... 73/64.42 |
| 6,037,592 | A  * | 3/2000 | Sunshine et al. ............. 250/343 |
| 6,391,096 | B1 * | 5/2002 | Waters ............... B01D 19/0031 73/19.02 |
| 6,526,805 | B1 * | 3/2003 | Babes-Dornea ... G01N 33/2841 73/19.12 |
| 7,239,977 | B2 * | 7/2007 | Fantana et al. ............... 702/185 |
| 7,391,035 | B2 | 6/2008 | Kong et al. |

(Continued)

OTHER PUBLICATIONS

Wiklund, Per et al., "Properties of Ageing Mineral Insulating Oils in Service" TechCon North America, 2012, pp. 1-19.

(Continued)

*Primary Examiner* — Peter Macchiarolo
*Assistant Examiner* — Jermaine Jenkins
(74) *Attorney, Agent, or Firm* — Baker & Hostetler LLP (57) ABSTRACT

A system and a process for detecting early stage electrical components problems with an analysis system is disclosed. The system process includes determining an oil quality of the oil of an electrical component using the analysis system. The system the process further including determining dissolved gases in the oil of the electrical component using the analysis system, processing and analyzing the oil quality and the dissolved gases using the analysis system, and determining whether there are problems in the electrical component using the analysis system.

19 Claims, 6 Drawing Sheets

(56) References Cited

U.S. PATENT DOCUMENTS

| | | | | |
|---|---|---|---|---|
| 7,647,202 | B2* | 1/2010 | Lamontagne | H02H 5/08 340/3.1 |
| 8,347,687 | B2* | 1/2013 | Cunningham | 73/19.11 |
| 8,616,045 | B2* | 12/2013 | Cavallini et al. | 73/19.11 |
| 8,704,634 | B2* | 4/2014 | Fantana et al. | 340/5.64 |
| 8,738,301 | B2* | 5/2014 | Frotscher et al. | 702/24 |
| 2009/0043538 | A1* | 2/2009 | Lamontagne | H01F 27/402 702/183 |
| 2013/0271166 | A1* | 10/2013 | Bouffard et al. | 324/750.01 |
| 2014/0025211 | A1* | 1/2014 | Cheim et al. | 700/286 |

OTHER PUBLICATIONS

"Maintenance of Liquid Insulation, Using Dielectric, Acid No., IFT, & Power Factor" excerpt from the United States Department of the Interior Bureau of Reclamation's Maintenance of Liquid Insulation: Mineral Oils and Askerals, Facilities Instructions, Standards & Techniques, vol. 3-4, 1992.

Duval, Michel, "The Dual Triangle For LTCs, Alternative Fluids and Other Applications", Doble Engineering Company, 2009, pp. 1-8.

"Serveron White Paper: DGA Diagnostic Methods", Serveron Corporation, 2007, pp. 1-12.

Griffin, Paul J. et al., "Load Tap Changer Diagnostics Using Oil Tests—A Key to Condition-Based Maintenance", Doble Engineering Company, 2005, pp. 1-21.

Delta-X Research Tech Notes, Technical Support Information for Delta-X Research Inc. Condition Assessment Software_com.

Perjanik, Nick, "Insulation Fluids: Sampling in the Field & Insulation Fluids: Quality Assessment Testing" Weidmann Diagnostic Solutions, 13th Annual Technical Conference, Nov. 10, 2014, pp. 1-75.

Jakob, Fredi, Dissolved Gas Analysis (Main Tank and LTC), Weidmann Diagnostic Solutions, Nov. 10, 2014, pp. 1-103.

Dominelli, Nick, "A New Approach to DGA Interpretation" Doble Engineering Company, 2004, pp. 1-18.

Part 3—What Makes a Good Insulating Oil Go Bad? pp. 179-187.

Establishing a Practical Oil Classification System, pp. 282-295.

Table 6.10 Basic Protective Maintenance Practice for Oil-Insulated Transformers pp. 816-817.

* cited by examiner

OIL QUALITY PARAMETERS LIMITS

| PARAMETER | DECREASING LEVEL | | | INCREASING LEVEL | | |
|---|---|---|---|---|---|---|
| | Caution 1 | Caution 2 | Caution 3 | Caution 1 | Caution 2 | Caution 3 |
| INTERFACIAL TENSION | 25 | 20 | 15 | | | |
| POWER FACTOR @25 | | | | 1 | | |
| COLOR | | | | 2 | 3 | 4 |
| PARTICLES > 100μm | | | | | 50 | 100 |
| ACIDITY | | | | 0.2 | 0.3 | 0.4 |
| DIELECTRIC BREAKDOWN (ASTM D1816) | | 20 | 12 | | | |
| FLUID QUALITY INDEX | | | | 8 | 15 | 22 |
| N2 / O2 | | | | 12 | 18 | 29 |

*FIG. 6*

SYSTEM AND PROCESS OF UTILIZING OIL QUALITY ANALYSIS AND DISSOLVED GAS ANALYSIS TO DETECT EARLY STAGE PROBLEMS IN OIL FILLED ELECTRICAL APPARATUSES

CROSS-REFERENCE TO RELATED APPLICATIONS

This application claims the benefit from U.S. Provisional Application No. 61/781,207 filed on Mar. 14, 2013, which is hereby incorporated by reference in its entirety for all purposes as if fully set forth herein.

FIELD OF THE INVENTION

The invention relates to a system and process of utilizing oil quality analysis and dissolved gas analysis to detect early stage problems in electrical components. More particularly, the invention relates to a system and process of utilizing oil quality analysis, dissolved gas analysis and an analysis process to detect early stage insulating oil degradation, formation of sludge and resistive contact filming, heating, coking and/or like problems in electrical components.

BACKGROUND OF THE INVENTION

It is well documented and widely accepted in the utility industry to use dissolved gas analysis (DGA) on dielectric insulating oil of power transformers, load tap changers, circuit breakers and voltage regulators as a tool for detecting problems and assessing an overall health of the oil insulated electrical apparatus. Oil quality analysis has been utilized as well with power transformers. Industry accepted published limits for DGA and oil quality currently exist for transformers (ref. IEEE C57.106). However, these prior approaches have failed to be applicable to other electrical components that include arcing, substantial exposure to humidity, moving parts, resistive contacts, and/or the like that result in insulating oil degradation, formation of sludge, resistive contact filming, heating, coking and/or like problems. Moreover these prior approaches typically only determine issues in the electrical components at a time period close to failure. For example, DGA applied to load tap changers has been recognized as a valid tool for detecting problems after a fault has already begun to occur in the load tap changer. Currently, utilities typically do not apply oil quality in conjunction with DGA for certain electrical components, such as load tap changers, and moreover there are no published industry accepted limits, available for certain electrical components such as load tap changers.

Additionally, with constantly decreasing budgets, utilities are faced with the need to extend maintenance cycles which require de-energized internal inspections while not reducing the reliability. This has resulted in a shift from time based to predictive based maintenance. While DGA is accepted as a diagnostic tool for identifying electrical components, such as load tap changers (LTCs) with internal faults, the detection occurs only if the oil is sampled and analyzed at the right time and after the internal fault has already developed. Using only DGA to determine LTCs already in failure mode leads to higher (reactive) maintenance costs, unplanned outages, and poor utilization of minimal maintenance personnel constantly "fighting fires."

Accordingly, there is a need for a system and process to more accurately detect early-stage problems with electrical components utilizing a new combination of analytical approaches.

SUMMARY OF THE INVENTION

The foregoing needs are met, to a great extent, by the invention, wherein in one aspect a technique and apparatus are provided that provides a system and process to detect early-stage issues with electrical components utilizing a new combination analysis approach.

In accordance with one aspect, a system for detecting early stage electrical component problems includes an oil quality analysis device configured to determine the oil quality of the oil of an oil filled electrical component, a dissolved gas analysis device configured to determine dissolved gases in the oil of the oil filled electrical component, and an analysis device configured to process and analyze the oil quality determined by the oil quality analysis device and the dissolved gases determined by the dissolved gas analysis device, the analysis device further configured to detect whether there are problems in the oil filled electrical component.

In accordance with another aspect, a system for detecting early stage electrical component problems includes a means for determining the oil quality of the oil of an electrical component, means for determining dissolved gases in the oil of the electrical component, and means for processing and analyzing the oil quality and the dissolved gases to detect whether there are problems in the electrical component.

In accordance with another aspect, a process for detecting early stage electrical component problems with an analysis system includes determining the oil quality of the oil of an electrical component using the analysis system, determining dissolved gases in the oil of the electrical component using the analysis system, processing and analyzing the oil quality and the dissolved gases using the analysis system, and determining whether there are problems in the electrical component using the analysis system.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the invention. It is important, therefore, that the claims be regarded as including such equivalent constructions insofar as they do not depart from the spirit and scope of the invention.

DETAILED DESCRIPTION

The invention will now be described with reference to the drawing figures, in which like reference numerals refer to like parts throughout. Embodiments of the invention advantageously provide a system and process to detect early-stage issues with electrical components utilizing a new combination of analytical approaches.

Electrical components may be filled with a fluid that serves several purposes. The fluid acts as a dielectric media, an insulator, and as a heat transfer agent. The fluid used in electrical components may be a mineral oil. Other types of fluids may include askerals, silicone type fluids, natural esters, and the like, hereinafter generically referred to as an insulating oil. The insulating oil may be in contact with numerous internal parts of the electrical component and evaluating dissolved gasses and performing oil quality analysis can reveal the faults, precursors of developing faults, or other issues with the electrical components that are a result of the natural aging processes of the oil. The dissolved gasses in the oil and the quality of the oil may be a result of problems inside the electrical components. Formation of the gases and changes in oil quality may be due to oxidation, vaporization, insulation decomposition, oil breakdown, formation of acids, electrolytic action, contamination from moisture (water), particles inside or migrating in from outside, and the like. Determination of the dissolved gases may be determined by a dissolved gas analysis (DGA) technique.

The DGA technique may involve extracting and/or stripping the gases from the oil and injecting them into a gas chromatograph (GC). Detection of gas concentrations may include the use of a flame ionization detector (FID), a thermal conductivity detector (TCD) and/or infrared spectrometry. The system may also employ a methanizer, which may convert any carbon monoxide and carbon dioxide present into methane so that the gas can be burned and detected with the FID. A multiple gas extractor may be utilized to sample oil by exposing it to vacuum numerous times. In the multiple gas extractor, a fixed volume oil sample may be drawn into a degassing vessel under vacuum, where the gases are released. These gases may be isolated to measure volume and may be transferred to the GC. Additionally, extraction of the gases may be achieved by agitating and heating the oil to release the gases that are then analyzed by the GC. The gases may be injected into the GC and transported through a column. The column may selectively retard the sample gases and they may be identified as the gases travel past a detector to produce a chromatogram. Other DGA techniques are contemplated as well and form part of the scope of the invention.

The gases extracted from the oil may be injected into the GC where the columns separate gases. The separated gases may be detected by the TCD for atmospheric gases, by the FID for hydrocarbons and oxides of carbon; and the methanator may be used to detect oxides of carbon.

Thermal faults may be detected by the presence of by-products of solid insulation decomposition; insulation overheating as a result of the electrical component generating more heat and deteriorating the insulation; insulation liquid overheating which results in breakdown of liquid by heat and formation of high thermal gases; corona discharge; arcing within the electrical component, formation of acids, complex oxides, and the like.

DGA results may include the concentration levels of each gas. Values for each of the gases may be trended over time so that the rate-of-change of the various gas concentrations can be evaluated. An increase in gas concentration and/or a trend in gas concentration may be indicative of a potential problem within the electrical component.

This invention further includes use of oil quality analysis together with DGA and applies an additional analysis to electrical components, such as free breathing LTCs, which are external to, and part of some power transformers and/or oil circuit breakers, voltage regulators, and other oil filled electrical equipment.

The process may be used to identify the potential for or the early stages of contact filming, heating, sludge formation, and/or the like and assess the condition of the electrical component, such as a LTC, without performing an internal inspection. Specifically, using DGA, oil quality analysis, and applying an analysis process which analyzes a nitrogen-oxygen ratio coupled with the oil acidity, interfacial tension, particle counts, oil color, oil power factor, dielectric breakdown, moisture content, or permittivity of oil, applying Duval triangle trending, applying discrete limits for DGA derived using IEEE C57.139 methodology and analyzing trending can identify electrical components, such as LTCs, in early stages of failure before damage to the electrical components or failure can occur.

Figure 1:
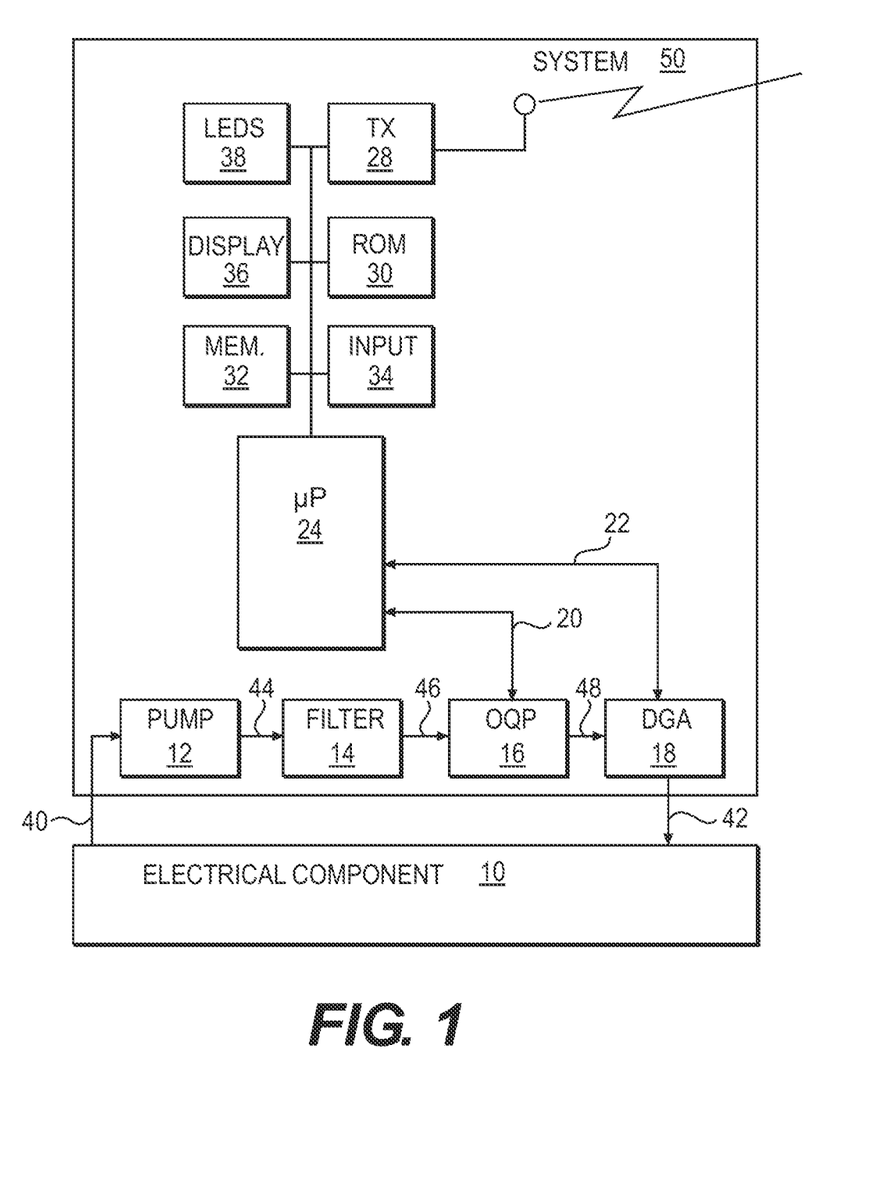
FIG. 1 shows an analysis system in accordance with one aspect of the invention.

FIG. 1 shows an analysis system in accordance with the invention. In particular, FIG. 1 shows an electrical component having an oil to be analyzed by an analysis system 50. The analysis system 50 may include a conduit 40 to sample the oil from the electrical component 10 from time to time as determined by the system 50. For example, the system 50 may determine to sample the oil from the electrical component 10 on a daily basis, weekly basis, in an ad hoc manner or the like. The conduit 40 may remove a portion of the oil from the electrical component 10 utilizing a pump 12 or similar fluid moving device. The oil may be sent from the pump 12 via a conduit 44 to a filter 14 in order to filter the oil and avoid damage to any other components of the system 50. The oil may exit the filter 14 via conduit 46 and enter an oil quality analysis device 16. The oil quality analysis device 16 may perform oil quality analyses on the oil as described herein and forward the results thereof along communication line 20 to a microprocessor 24. The oil in the oil quality analysis device 16 may exit along a conduit 48 and may enter a dissolved gas analysis device 18. Within the dissolved gas analysis device 18, the dissolved gases in the oil may be determined and the results of the determination may be communicated along communication line 22 to the microprocessor 24. Thereafter, the oil may be returned to the electrical component 10 along a conduit 42 or discarded. It is within the scope and spirit of the invention to incorporate the system 50 into current electrical components in any number of ways including as part of a filter unit or filtration system of an electrical component. The system 50 may also be a standalone component or system 50 may also be a transportable self-contained unit.

The system 50 may include a memory 32 to store an operating system together with one or more applications for analyzing the oil quality analysis received from the oil quality analysis device 16 and analyzing the dissolved gas analysis received from the dissolved gas analysis device 18. The memory 32 may further include the ability to store analysis, data for trending over time, and the like as needed for the system 50.

The system 50 may further include a read-only memory 30 to provide the basic memory functionality such as the storage of firmware or the like. The system 50 may further include a display 36, such as a LCD, LED, or the like, to provide a user or maintenance personnel with information, data, various operating details, and the like of the system 50. The system 50 may further include an input device 34 such as a keyboard, keypad, USB connector, mouse input, FireWire input, or the like for providing input to the system 50 or the microprocessor 24. The system 50 may further include various operating lights, such as LEDs 38, to indicate the operating condition of the system 50, communication status of the system 50, power status of the system 50, or the like.

The system 50 may further include a transmitter 28. The transmitter 28 may use a communication channel such as a wireless fidelity protocol communication channel, cellular data protocol communication channel, or the like to transmit various statuses, data, alarms, and conditions of the system 50. Of course the transmitter 28 may include a hardwired connection instead of or in addition to the wireless connections. The transmitter 28 may include all additional structure in order to provide transmission capability including a universal asynchronous receiver transmit circuit, RS-232 and the like. Additionally, the transmitter 28 may transmit the results of the oil quality analysis and the dissolved gas analysis performed by the microprocessor 24.

Figure 2:
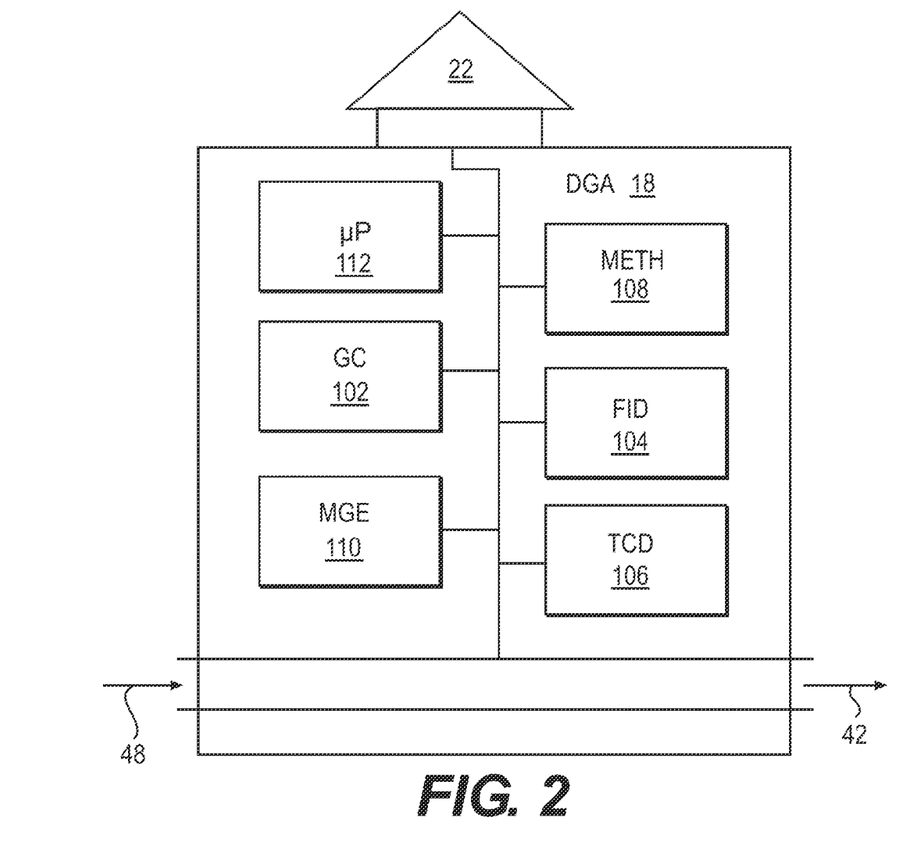
FIG. 2 shows a dissolved gas analysis device in accordance with one aspect of the invention.

FIG. 2 shows a dissolved gas analysis device in accordance with the invention. In particular, FIG. 2 shows an exemplary construction of the dissolved gas analysis device 18. More specifically, the dissolved gas analysis device 18 may involve extracting and/or stripping the gases from the oil received from the conduit 48 and injecting them into a gas chromatograph (GC) 102 or multiple gas solid-state sensors. Detection of gas concentrations may include the use of a flame ionization detector (FID) 104 and/or a thermal conductivity detector (TCD) 106. The system may also employ a methanizer (METH) 108, which may convert any carbon monoxide and carbon dioxide present into methane so that the gas can be burned and detected with the FID 104. The dissolved gas analysis device 18 may further include a multiple gas extractor (MGE) 110 that may sample oil by exposing it to vacuum numerous times. The dissolved gas analysis device 18 may include any other additional structure to provide this functionality including analog-to-digital converters, microprocessor 112, communication devices, and the like. The dissolved gas analysis device 18 may also include multiple or single specific solid-state gas sensors identifying gas concentrations and converting the concentration to electrical signals such as 0-1 mA or 4-20 mA to be received by the system 50.

Figure 3:
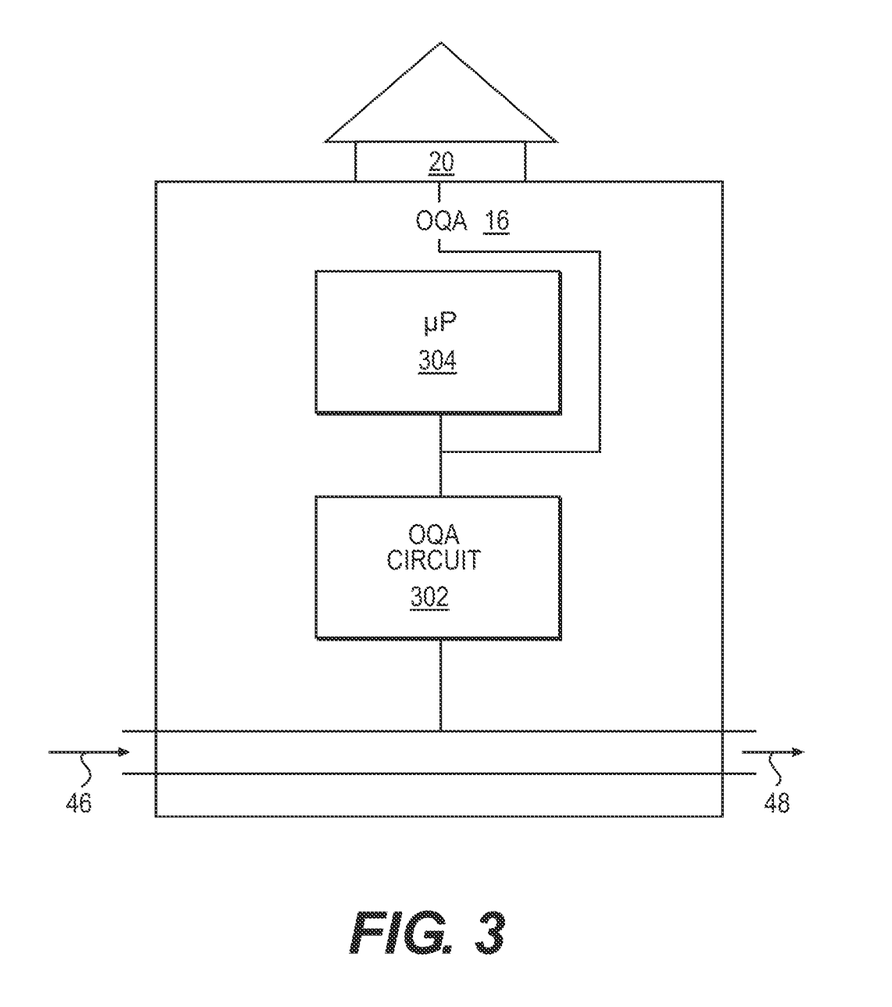
FIG. 3 shows an oil quality analysis device in accordance with one aspect of the invention.

FIG. 3 shows an oil quality analysis device in accordance with the invention. In particular, FIG. 3 shows an exemplary construction of the oil quality analysis device 16. The oil quality analysis device 16 may include an oil quality analysis circuit 302. The oil quality analysis circuit 302 may receive the oil input through conduit 46 and perform various oil quality analyses on the oil including determining oil acidity, determining interfacial tension, determining particle counts, and the like. The oil quality analysis process may include solid-state devices or optical devices to measure IFT, acidity, dielectric breakdown, power factor, color, moisture content, resistivity of the oil, and permittivity of the oil. The oil quality analysis device 16 may include any other additional structure to provide this functionality including analog-to-digital converters, microprocessor 304, communication devices, and the like.

Figure 4:
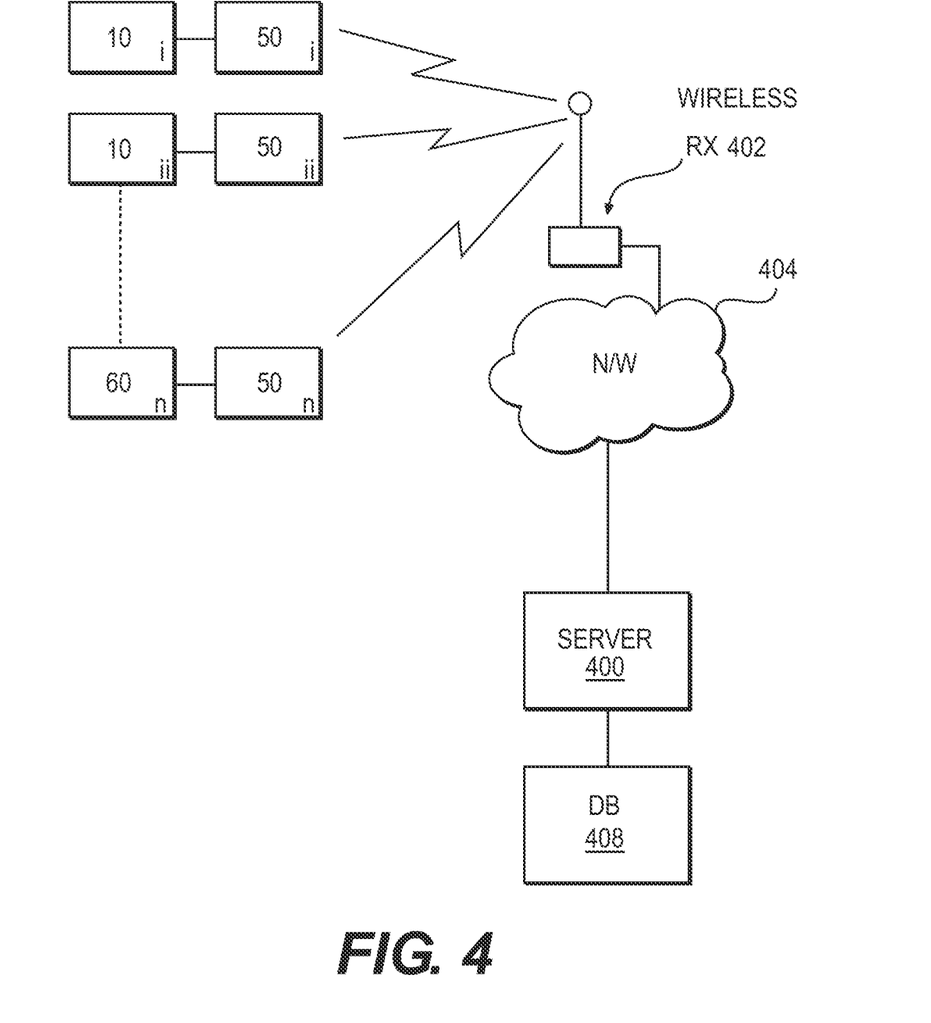
FIG. 4 shows a system for monitoring a plurality of analysis systems in accordance with one aspect of the invention.

FIG. 4 shows a system for monitoring a plurality of analysis systems. In particular, FIG. 4 shows a series of electrical components 10 (*i-n*) and systems 50 (*i-n*) analyzing the oil within the electrical components 10. The systems 50 may each include a transmitter 28 as described above. The transmitter 28 may communicate with a transmitter 402 along a communication channel, such as a wireless access point using a wireless fidelity protocol, a cellular data transmitter, or the like, to receive data from each of the systems 50 of FIG. 4. The data may then be placed on a network 404 such as a wireless network, the Internet, intranet, cloud storage, or the like to transmit the data to a computer generically referred to herein as a server 406. The server 406 may subsequently store the data in a database 408. The server 406 and database 408 may monitor the data and generate alarms and/or reports regarding the condition of the oil in each of electrical components 10, the status of the systems 50, recommend further testing, or the need to perform maintenance, or the like. Additionally, the above described functionalities of the microprocessor 24 and the server 406 may be handled exclusively by either or shared in different ways.

Figure 5:
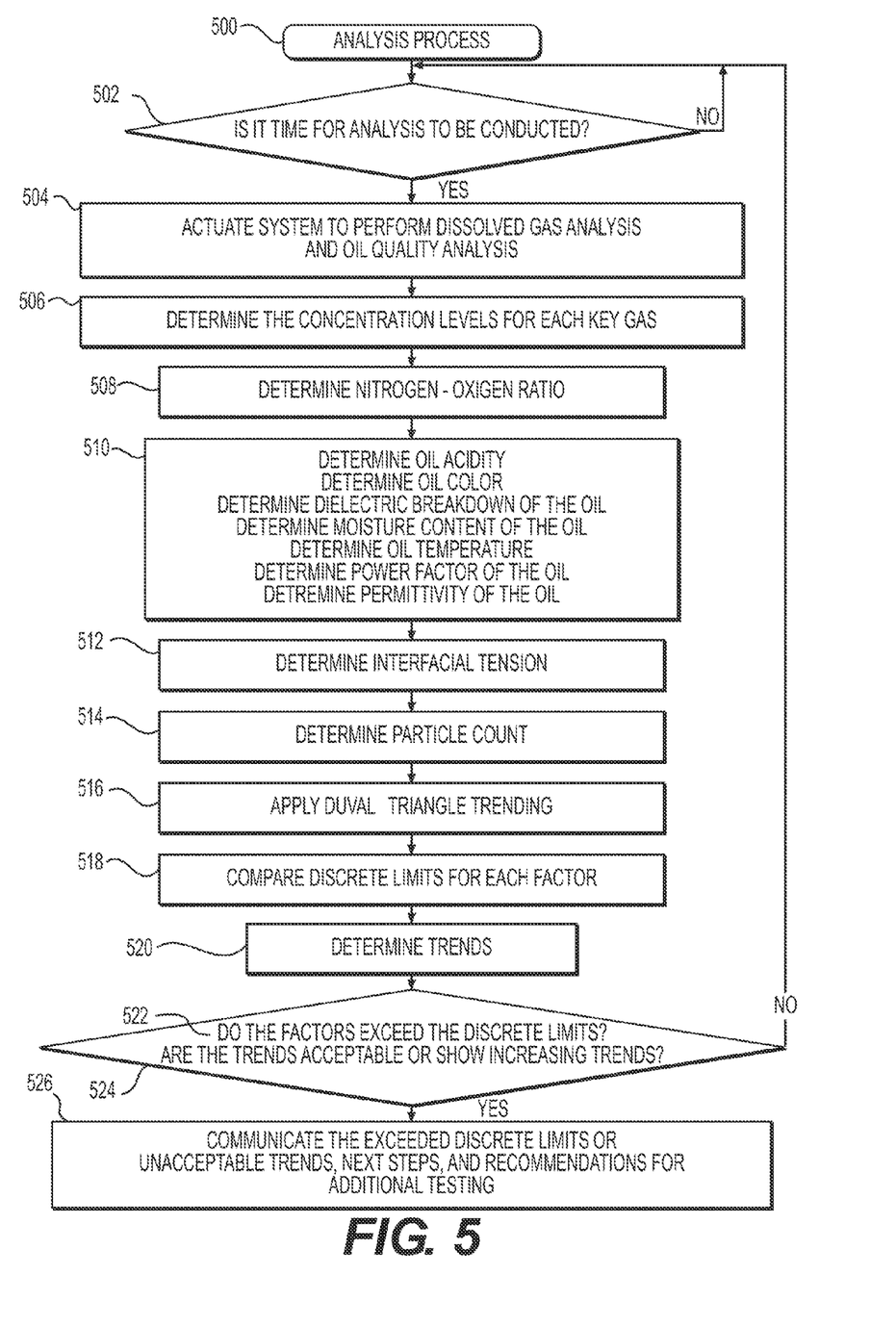
FIG. 5 shows a process of analyzing fluid in accordance with one aspect of the invention.

FIG. 5 shows a process of analyzing oil in accordance with the invention. In particular, FIG. 5 shows an analysis process 500 that may be executed by the system 50 and/or the server 406. In particular the microprocessor 24 may take active steps to execute the process as described in conjunction with FIG. 5.

The process may be performed continuously or discreetly. In this regard, the process 500 may execute hourly, daily, weekly, or periodically using any timeframe. The process 500 may also execute in an ad hoc manner as requested by a user or in response to prior executions of the process 500. For example, if the analysis is indicating results that are unfavorable, the process 500 may be executed more frequently in the future. As shown in 502, the process 500 determines whether it is time for analysis to be conducted. If no, the process 500 may simply loop and wait until it is time to execute the process 500. If yes, the process 500 may advance to perform the process. It is within the scope and spirit of the invention that the order of the process 500 may be changed, not all the steps need to be performed, and additional steps may be included.

Next, the process 500 performs dissolved gas analysis and oil quality analysis as shown in 504. For example, the dissolved gas analysis may be performed by the system 50 utilizing the dissolved gas analysis device 18; and the oil quality analysis may be performed by the system 50 utilizing the oil quality analysis device 16. The process 504 may be conducted serially in no particular order. Alternatively the process 504 made be conducted in parallel. Moreover, the process 504 may further include an assignment of a code indicative of the condition of the dissolved gases and a condition code associated with oil quality. Additionally, the codes may be prioritized and ranked based on a combined code for communication in conjunction with 526 below.

The results of the dissolved gas analysis and the oil quality analysis may be further analyzed to determine the concentration levels for each gas as shown in 506 for early detection of formation of sludge deposits in the oil and/or formation of resistive film deposits on electrical contacts that lead to contact heating and/or coking failures. The results may be further analyzed to determine a nitrogen-oxygen ratio as shown in 508. Additionally, the nitrogen-oxygen ratio being determined to be undesirable may be indicative of a plugged breather. Accordingly, as part of process 526, the indication of a possibly plugged breather may be communicated to the user for scheduled maintenance.

The results may further be analyzed to determine one or more of oil acidity, oil color, dielectric breakdown of the oil, moisture content of the oil, oil temperature, power factor of the oil, permittivity of the oil, as shown in 510, may be further analyzed to determine an interfacial tension as shown in 512, may be further analyzed to determine a particle count as shown in 514, may be further analyzed to determine power factor, moisture content, dielectric breakdown, color, permittivity of oil, and the like.

Based on the analysis set forth in 504, 506, 508, 510, 512, and/or 514 and the like, the results may be subjected to a Duval triangle analysis as shown in 516. In particular, concentrations of various gases such as methane, ethylene, and acetylene may be expressed as percentages and plotted as a point in a triangular coordinate system subdivided into fault zones and movement in the Duval triangle trended over time. The fault zone in which the point is located and/or direction of movement in the triangle may define a likely fault type which produced the particular gas concentrations and may provide an indication that the fault is progressively becoming worse. A plurality of results subjected to the Duval triangle analysis can be stored and analyzed to determine trends. Additionally, calculation of fluid quality index (FQI) may be calculated and subsequently compared to discrete limits.

Additionally, as shown in 518, each of the results of 504, 506, 508, 510, 512, 514, 516, and/or the like may be compared to discrete limits for each factor that may be pre-determined and/or set by the end user. These discrete limits may be stored in the memory 32 and updated from time to time. Furthermore, as shown in 520, each of these factors may be stored and the subsequent results may be analyzed to determine trends and/or rolling trends looking at specific historical time frames, such as days, weeks, months, years, and the like.

As shown in 522, when the factors do not exceed the discrete limits and the trends are acceptable as shown in 524, the analysis process 500 may end and loop back to the beginning of the process and await the next time the analysis process is to be conducted. On the other hand, if the factors exceed the discrete limits 522 or the trends are not acceptable as shown in 524, the process will move to 526 and communicate the exceeded discrete limits and/or communicate the unacceptable trends, possible recommendations for further testing to confirm equipment condition, or for planning for future scheduled maintenance. The communication of the data may be to the display 36 of the system 50, to the LEDs 38 of the system 50, may be transmitted by the transmitter 28 of the system 50 and/or the like. Alternatively, the process 500 may be conducted in the server 406 with the data required being transmitted from the system 50 by the transmitter 28. The communication may further be forwarded to any user, computer, or entity as desired via e-mail, SMS text message, Web application, or the like. Such communication may include any of the aforementioned data, status, alarms, next steps, recommendations, or the like.

Figure 6:
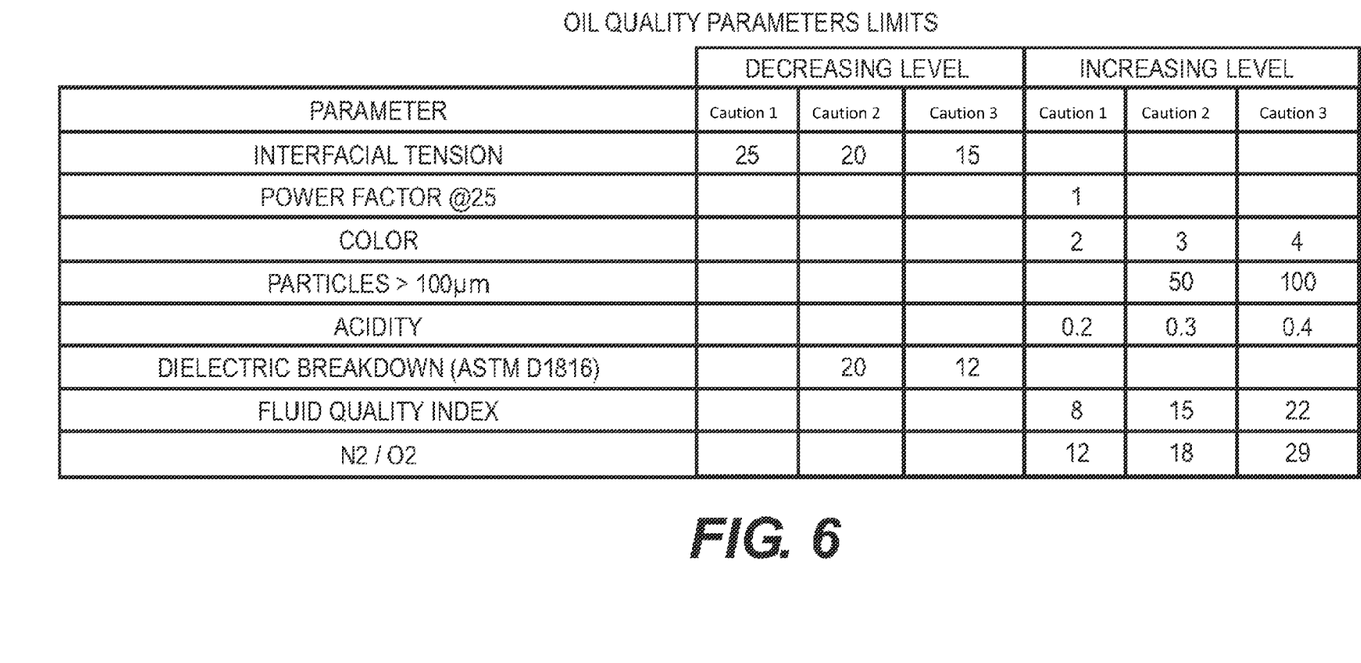
FIG. 6 shows a partial table of exemplary oil quality and gas analysis parameters in accordance with one aspect of the invention.

FIG. 6 shows a partial table of exemplary oil quality and gas analysis parameters according to the invention. In this regard, the left column shows the various parameters being analyzed, and the right six columns indicate the various factors that may result in an alert, warning, or alarm. In conjunction with steps 522 and 524, the system may compare the various factors determined with those listed in the table of FIG. 6. If the various factors meet the listed criteria, the step of communicating 526 may provide a communication that includes an alert, warning, or alarm as indicated.

Accordingly, use of this invention will provide a means for very early detection of potential failures or identification of electrical components trending towards failure and in need of maintenance within the next 12 months. Detection of such issues in LTCs long before damage can occur saves extensive repair costs and emergency (unplanned) outages. In addition this will facilitate better utilization of electrical components for customers.

The invention may include communication channels that may be any type of wired or wireless electronic communications network, such as, e.g., a wired/wireless local area network (LAN), a wired/wireless personal area network (PAN), a radiofrequency identification device (RFID), mesh network, wired/wireless home area network (HAN), a wired/wireless wide area network (WAN), a campus network, a metropolitan network, an enterprise private network, a virtual private network (VPN), an internetwork, a backbone network (BBN), a global area network (GAN), the Internet, an intranet, an extranet, an overlay network, a cellular telephone network, a Personal Communications Service (PCS), using known protocols such as the Global System for Mobile Communications (GSM), CDMA (Code-Division Multiple Access), W-CDMA (Wideband Code-Division Multiple Access), Wireless Fidelity (Wi-Fi), Bluetooth, Long Term Evolution (LTE), EVolution-Data Optimized (EVDO) and/or the like, and/or a combination of two or more thereof.

The invention may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

In an embodiment, the invention may be web-based. For example, the server 406 may operate a web application to allow the invention to operate in conjunction with a database. The web application may be hosted in a browser-controlled environment (e.g., a Java applet and/or the like), coded in a browser-supported language (e.g., JavaScript combined with a browser-rendered markup language (e.g., Hyper Text Markup Language (HTML) and/or the like)) and/or the like such that any computer running a common web browser (e.g., Internet Explorer™, Firefox™, Chrome™, Safari™ or the like) may render the application executable from a remote location. A web-based service may be more beneficial due to the ubiquity of web browsers and the convenience of using a web browser as a client (i.e., thin client). Further, with inherent support for cross-platform compatibility, the web application may be maintained and updated without distributing and installing software on each.

Further in accordance with various embodiments of the invention, the methods described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein.

It should also be noted that the software implementations of the invention as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the invention is considered to include a tangible storage medium or distribution medium, as listed herein and including art-recognized equivalents and successor media, in which the software implementations herein are stored.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

The invention claimed is:

1. A system for detecting early stage electrical component problems comprising:
   an oil quality analysis device configured to determine an oil quality of an oil of an electrical component in response to periodic sampling;
   a dissolved gas analysis device configured to determine dissolved gases in the oil of the electrical component in response to periodic sampling; and
   an analysis device configured to process and analyze the oil quality determined by the oil quality analysis device and the dissolved gases determined by the dissolved gas analysis device, the analysis device further configured to determine whether there are problems in the electrical component based on predetermined user configurable parameters,
   wherein the analysis device is further configured to determine a trend in at least one of the quality of the oil and the dissolved gases in the oil;
   wherein the analysis device is further configured to determine whether at least one of the quality of the oil and the dissolved gases in the oil exceed discrete limits and/or show an increasing trend; and
   wherein the analysis device is further configured to at least one of communicate and notify when at least one of the trend is unacceptable and when discrete limits have been exceeded.

2. The system according to claim 1 wherein the dissolved gas analysis device comprises at least one of a gas chromatograph, flame ionization detector, a thermal conductivity detector, a methanizer, at least one specific solid-state gas sensor, and a multiple gas extractor.

3. The system according to claim 1 wherein the dissolved gas analysis device is configured to determine at least one of concentration levels of gas and a nitrogen-oxygen ratio.

4. The system according to claim 1 wherein the oil quality analysis device is configured to determine at least one of an acidity of the oil, an interfacial tension of the oil, a particle count in the oil, permittivity of the oil, oil color, dielectric breakdown, power factor, and moisture content.

5. The system according to claim 1 wherein the analysis device is further configured to determine a trend in at least one of the quality of the oil and the dissolved gases in the oil.

6. The system according to claim 1 wherein the analysis device is further configured to determine a rolling trend looking at a specific historical period of time including one of days, weeks, months, and years.

7. The system according to claim 1 wherein the analysis device is further configured to determine whether at least one of the quality of the oil and the dissolved gases in the oil exceed discrete limits.

8. The system according to claim 1 further comprising a communication device configured to communicate at least one of data, a status, the problems, recommended next steps and additional testing to confirm the electrical component condition over a communication channel.

9. A monitoring system comprising the system for detecting early stage electrical component problems of claim 1 further comprising:
   a communication channel to communicate with the system for detecting early stage electrical components problems.

10. The system according to claim 1 wherein the dissolved gas analysis device is configured to determine concentration levels of gas and a nitrogen-oxygen ratio.

11. The system according to claim 1 wherein the oil quality analysis device is configured to determine an acidity of the oil, an interfacial tension of the oil, a particle count in the oil, permittivity of the oil, oil color, dielectric breakdown, power factor, and moisture content.

12. The system according to claim 1 wherein the analysis device is further configured to determine a trend in the quality of the oil and the dissolved gases in the oil.

13. The system according to claim 1 wherein the analysis device is further configured to determine whether the quality of the oil and the dissolved gases in the oil exceed discrete limits.

14. A process for detecting early stage electrical component problems with an analysis system comprising:
   determining an oil quality of an oil of an electrical component in response to periodic sampling using the analysis system;
   determining dissolved gases in the oil of the electrical component in response to periodic sampling using the analysis system;
   processing and analyzing the oil quality and the dissolved gases using the analysis system;
   determining whether there are problems in the electrical component using the analysis system based on predetermined parameters;
   determining a trend in at least one of the quality of the oil and the dissolved gases in the oil;
   determining whether at least one of the quality of the oil and the dissolved gases in the oil exceed discrete limits; and
   communicating when at least one of the trend is unacceptable and when discrete limits have been exceeded.

15. The process according to claim 14 further comprising communicating at least one of data, a status, and the problems in the electrical components over a communication channel.

16. The process according to claim 14 further comprising:
   monitoring a plurality of analysis systems;
   communicating with the plurality of analysis systems; and reporting information related to the monitoring and communicating.

17. The process according to claim 14 further comprising communicating data, a status, and the problems in the electrical components over a communication channel.

18. The process according to claim 14 further comprising:
determining a trend in the quality of the oil and the dissolved gases in the oil;
determining whether the quality of the oil and the dissolved gases in the oil exceed discrete limits; and
communicating when at least one of the trend is unacceptable and when discrete limits have been exceeded.

19. The process according to claim 18 further comprising:
monitoring a plurality of analysis systems;
communicating with the plurality of analysis systems; and
reporting information related to the monitoring and communicating.

* * * * *